United States Patent
Yamasaka et al.

(10) Patent No.: US 11,944,266 B2
(45) Date of Patent: Apr. 2, 2024

(54) ENDOSCOPE

(71) Applicant: OLYMPUS CORPORATION, Tokyo (JP)

(72) Inventors: Daichi Yamasaka, Chofu (JP); Hidetada Sueyasu, Hino (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 670 days.

(21) Appl. No.: 17/113,482

(22) Filed: Dec. 7, 2020

(65) Prior Publication Data

US 2021/0106213 A1 Apr. 15, 2021

Related U.S. Application Data

(63) Continuation of application No. PCT/JP2019/008372, filed on Mar. 4, 2019.

(30) Foreign Application Priority Data

Jun. 8, 2018 (JP) .................................. 2018-110118

(51) Int. Cl.
*A61B 1/00* (2006.01)
*A61B 1/005* (2006.01)
*A61B 1/018* (2006.01)

(52) U.S. Cl.
CPC ...... *A61B 1/00098* (2013.01); *A61B 1/00042* (2022.02); *A61B 1/00148* (2022.02); (Continued)

(58) Field of Classification Search
CPC . A61B 1/0056; A61B 1/0057; A61B 1/00098; A61B 1/018
See application file for complete search history.

(56) References Cited

U.S. PATENT DOCUMENTS 5,569,157 A * 10/1996 Nakazawa ......... A61B 1/00177
600/106
6,527,706 B2 * 3/2003 Ide ....................... A61B 1/0057
600/142

(Continued)

FOREIGN PATENT DOCUMENTS

JP S56-8030 A 1/1981
JP H07-184826 A 7/1995

(Continued)

OTHER PUBLICATIONS

International Search Report dated May 28, 2019 issued in PCT/JP2019/008372.

*Primary Examiner* — Matthew J Kasztejna
(74) *Attorney, Agent, or Firm* — Scully, Scott, Murphy & Presser, P.C.

(57) ABSTRACT

An endoscope includes: an outer cylinder including an outer cylinder distal end portion held by a distal end holding portion provided inside an insertion section and an outer cylinder proximal end portion held by a proximal end holding portion provided on a proximal end side relative to the distal end holding portion; and an inner cylinder provided inside the outer cylinder, the inner cylinder including inside a wire coupled to a movable portion provided in the insertion section, an amount of stretch of the inner cylinder due to bending of the insertion section being larger than an amount of stretch of the outer cylinder due to the bending, the inner cylinder, in a stretch state where the inner cylinder stretches due to the bending, forming a gap in a longitudinal direction of the outer cylinder between the inner cylinder and the proximal end holding portion.

20 Claims, 11 Drawing Sheets

(52) U.S. Cl.
CPC ............ *A61B 1/0056* (2013.01); *A61B 1/018* (2013.01); *A61B 1/0008* (2013.01)

(56) References Cited

U.S. PATENT DOCUMENTS

| | | | | |
|---|---|---|---|---|
| 6,582,357 | B2* | 6/2003 | Ouchi | A61B 1/00177 |
| | | | | 600/134 |
| 6,587,227 | B1* | 7/2003 | Fullerton | H04N 1/00811 |
| | | | | 399/362 |
| 6,887,195 | B1* | 5/2005 | Pilvisto | A61B 1/0055 |
| | | | | 600/141 |
| 7,591,783 | B2* | 9/2009 | Boulais | A61B 1/0008 |
| | | | | 600/141 |
| 8,591,404 | B2* | 11/2013 | Yamazaki | A61B 1/0057 |
| | | | | 600/149 |
| 2004/0242966 | A1* | 12/2004 | Barry | A61B 1/0057 |
| | | | | 600/146 |
| 2006/0200000 | A1* | 9/2006 | Sato | A61B 1/0057 |
| | | | | 600/146 |
| 2007/0299311 | A1* | 12/2007 | Sato | A61B 1/00071 |
| | | | | 600/149 |
| 2009/0240110 | A1* | 9/2009 | Miyawaki | A61B 1/0055 |
| | | | | 600/149 |
| 2010/0168519 | A1* | 7/2010 | Matsuo | A61B 1/0055 |
| | | | | 600/139 |
| 2018/0140171 | A1* | 5/2018 | Yamaya | A61B 1/00062 |

FOREIGN PATENT DOCUMENTS

| | | |
|---|---|---|
| JP | 2002-291685 A | 10/2002 |
| JP | 2009-78012 A | 4/2009 |

* cited by examiner

ENDOSCOPE

CROSS REFERENCE TO RELATED APPLICATION

This application is a continuation application of PCT/JP2019/008372 filed on Mar. 4, 2019 and claims benefit of Japanese Application No. 2018-110118 filed in Japan on Jun. 8, 2018, the entire contents of which are incorporated herein by this reference.

BACKGROUND OF THE INVENTION

1. Field of the Invention

The present invention relates to an endoscope in which a treatment instrument raising base configured to raise a treatment instrument or the like in an affected site direction is provided at a distal end portion of an insertion section.

2. Description of the Related Art

A typical endoscope includes a guide mechanism such as a treatment instrument raising device configured to raise a treatment instrument, which is inserted in an insertion section through a treatment instrument insertion opening, by using a treatment instrument raising base provided in a distal end member of the insertion section to guide the treatment instrument to a treatment site in a subject. By virtue of a wire advancing/retracting mechanism connected to an operation knob through a wire extending in a guide tube from the insertion section to an operation section, the treatment instrument raising base is raised or brought down with advancement/retraction of the wire according to an operation of the operation knob. After being used in the subject, the treatment instrument raising base and the wire are removed from the endoscope and cleaned. After being cleaned, the treatment instrument raising base and the wire are attached to the endoscope again.

For example, Japanese Patent Application Laid-Open Publication No. 7-184826 discloses an endoscope including a removable wire. A user press-fixes the wire by removing a protection cover provided on the endoscope to expose a pressing portion and rotating the pressing portion by using the removed protection cover as a tool to tighten the pressing portion.

SUMMARY OF THE INVENTION

An endoscope according to an aspect of the present invention includes the following: an outer cylinder including an outer cylinder distal end member held by a distal end holding member provided inside an insertion section and an outer cylinder proximal end member held by a proximal end holding member provided on a proximal end side relative to the distal end holding member; and an inner cylinder provided inside the outer cylinder, the inner cylinder including inside a wire coupled to a movable member provided in the insertion section, an amount of stretch of the inner cylinder due to bending of the insertion section being larger than an amount of stretch of the outer cylinder due to the bending, the inner cylinder, in a stretch state where the inner cylinder stretches due to the bending, forming a gap in a longitudinal direction of the outer cylinder between the inner cylinder and the proximal end holding member. The movable member includes a treatment instrument raising base provided on a distal end side of the insertion section and configured to change an orientation of a distal end side of a treatment instrument inserted in the insertion section, and the wire is configured to be advanced or retracted by an external operation to raise or bring down the treatment instrument raising base.

DETAILED DESCRIPTION OF THE PREFERRED EMBODIMENTS

Description will be made below on an embodiment of the present invention with reference to the drawings.

(Configuration of Endoscope 1)

Figure 1:
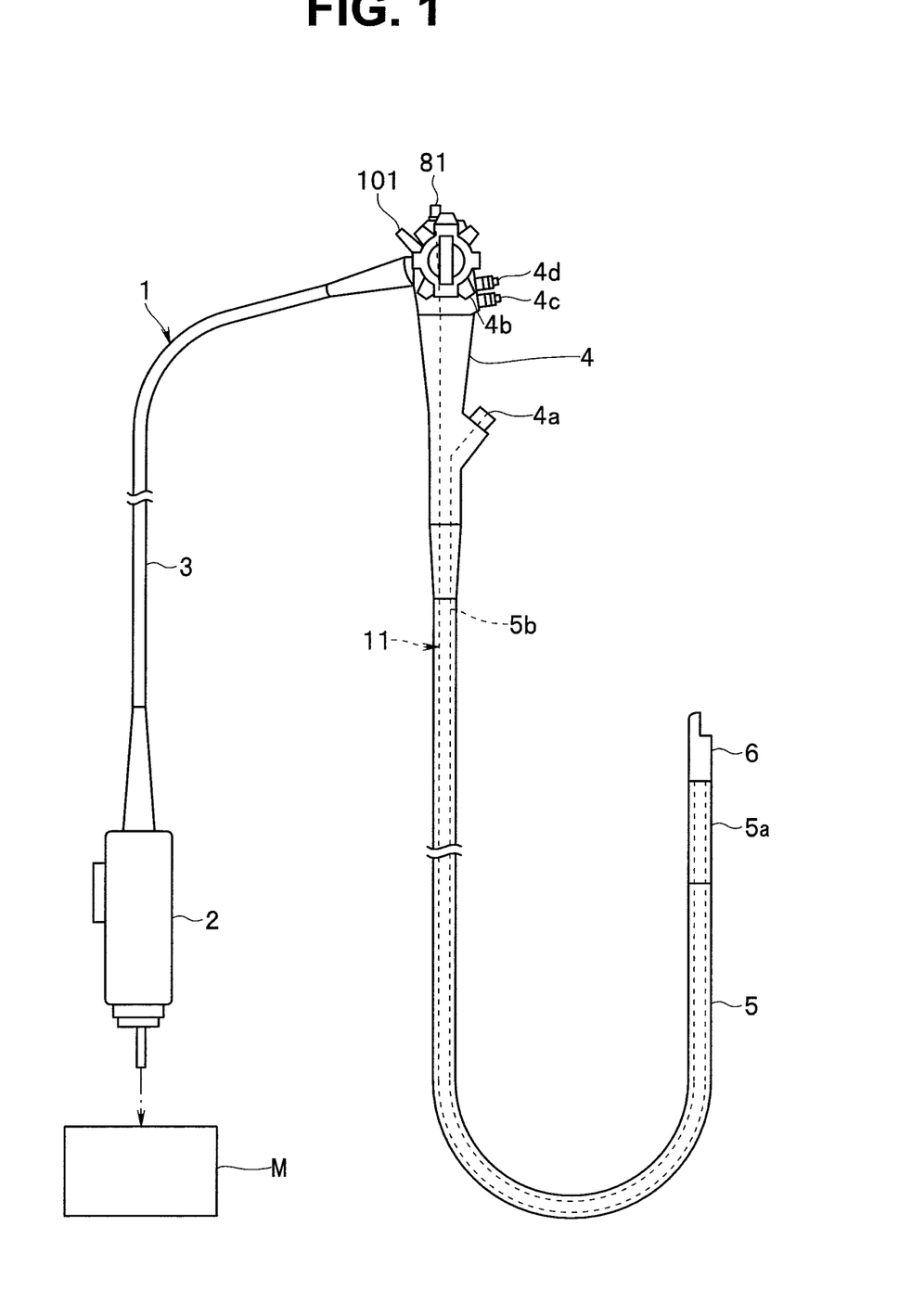
FIG. 1 is a diagram showing an example of a configuration of an endoscope according to an embodiment of the present invention.
Figure 2:
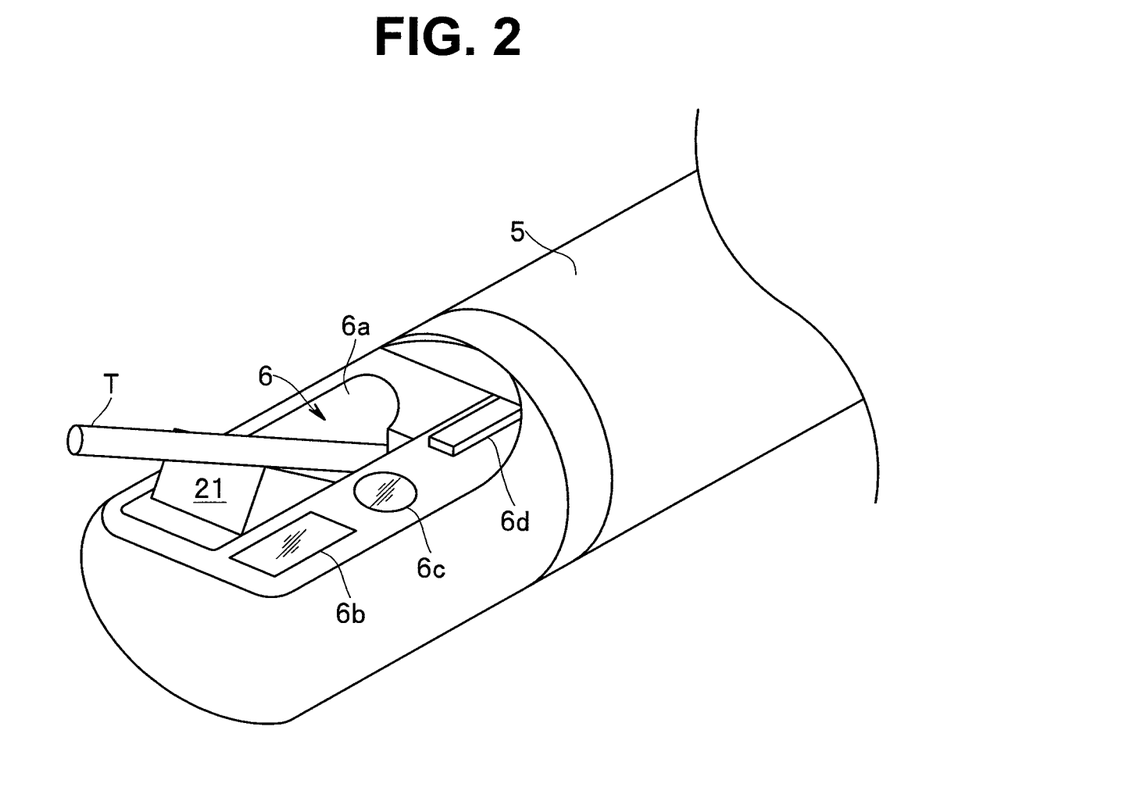
FIG. 2 is a diagram showing an example of a configuration of a distal end member of an insertion section of the endoscope according to the embodiment of the present invention.

FIG. 1 is a diagram showing an example of a configuration of an endoscope 1 according to an embodiment of the present invention. FIG. 2 is a diagram showing an example of a configuration of a distal end member 6 of an insertion section 5 of the endoscope 1 according to the embodiment of the present invention.

The endoscope 1 includes a scope connector 2, a universal cord 3 extending from the scope connector 2, an operation section 4 attached to the universal cord 3, an insertion section 5 provided continuous with a distal end side of the operation section 4, and a distal end member 6 provided at a distal end portion of the insertion section 5.

The scope connector 2 is configured to be connected to an endoscope device body M such as a power source and a control device.

The universal cord 3, in which various conduits, signal lines, and optical fibers are provided, connects the scope connector 2 and the operation section 4 to each other.

The operation section 4 is configured to be able to perform various operations of the endoscope 1. The operation section 4 includes a treatment instrument insertion opening 4a, an angle knob 4b, an air/water feeding button 4c, and a suction button 4d.

A treatment instrument T (FIG. 2), which is to be introduced from the distal end member 6, can be inserted through the treatment instrument insertion opening 4a. The treatment instrument T is, for example, forceps.

The angle knob 4b is connected to a bending portion 5a of the insertion section 5 through a wire for bending. The angle knob 4b enables inputting instructions from a user for bending the bending portion 5a.

The air/water feeding button 4c enables inputting instructions from the user for feeding air or a liquid into a nozzle 6d of the distal end member 6 from the endoscope device body M.

The suction button 4d enables inputting instructions from the user for sucking a suction target into the endoscope device body M through an opening portion 6a of the distal end member 6.

The insertion section 5, which is elongated, is configured to be insertable into a lumen in a subject. The insertion section 5 includes the bending portion 5a and a treatment instrument conduit 5b.

The bending portion 5a includes an outer peripheral portion formed of, but not limited to, an elastic member such as rubber. The bending portion 5a, which is provided near the distal end member 6, is bent as a result of a bending wire being pulled in accordance with an operation of the angle knob 4b. The bending portion 5a may include a bending piece group inside, the bending piece group including a plurality of short-cylindrical bending pieces that are provided continuous in the longitudinal direction and relatively rotatable.

The treatment instrument conduit 5b is provided inside the insertion section 5 to receive the treatment instrument T, causing the treatment instrument insertion opening 4a and the distal end member 6 to communicate with each other.

Note that various conduits or signal lines are provided inside the insertion section 5 in addition to the treatment instrument conduit 5b.

As shown in FIG. 2, the distal end member 6 includes a hard member. The distal end member 6 includes the opening portion 6a, an illumination window 6b, an observation window 6c, and the nozzle 6d.

The opening portion 6a is provided in an outer peripheral portion of the distal end member 6. The opening portion 6a is communicates with the treatment instrument conduit 5b.

A subject is irradiated with illumination light delivered from a light source in the endoscope device body M through the illumination window 6b.

Return light from the subject is let in through the observation window 6c, being projected onto an unshown image pickup device. The image pickup device is configured to convert the return light to an image pickup signal and output the image pickup signal to the endoscope device body M.

The nozzle 6d is configured to discharge a gas or a liquid fed by the endoscope device body M.

(Configuration of Guide Mechanism 11)

Subsequently, description will be made on a configuration of a guide mechanism 11.

Figure 3:
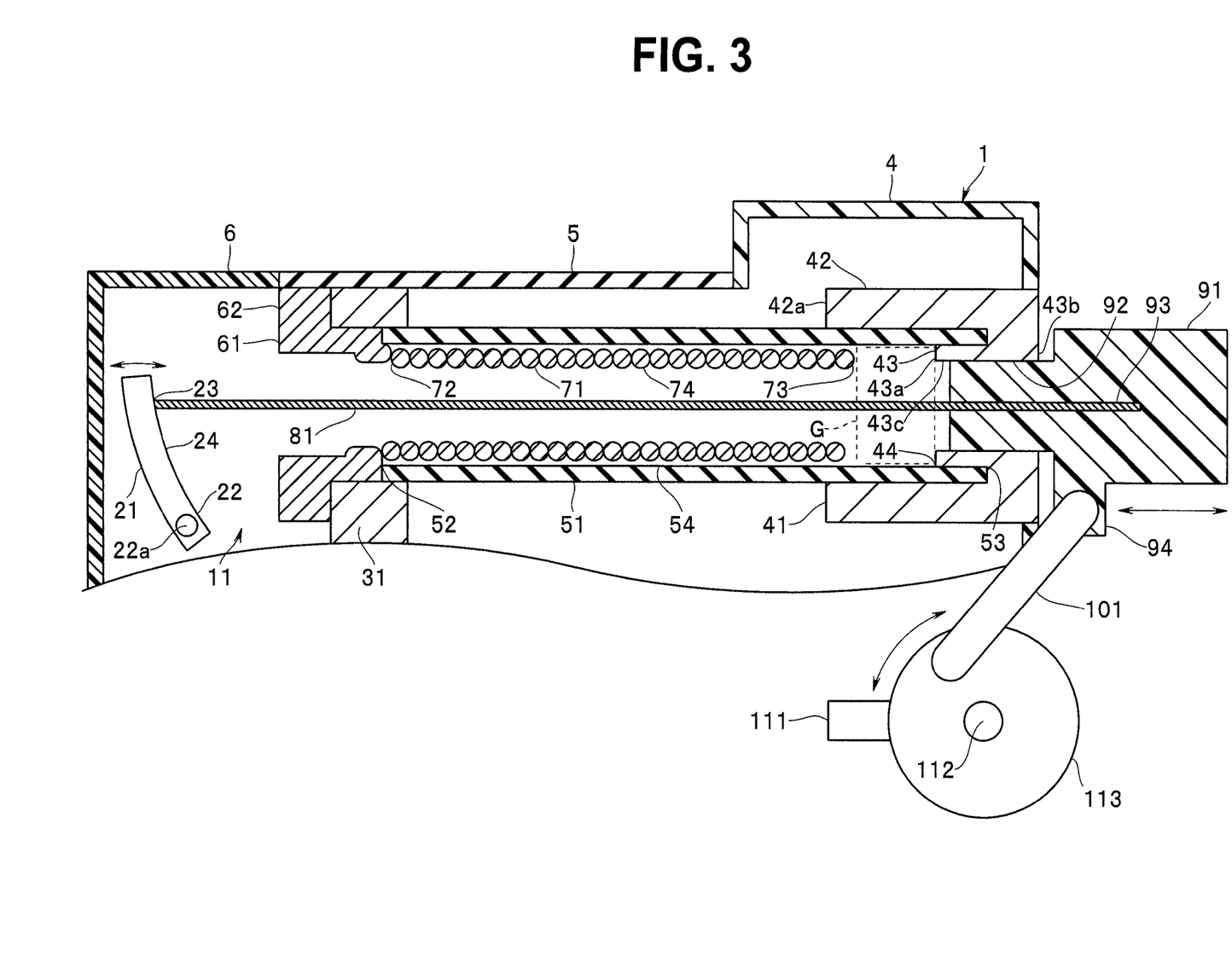
FIG. 3 is a diagram showing an example of a configuration of a guide mechanism of the endoscope according to the embodiment of the present invention.

FIG. 3 is a diagram showing an example of the configuration of the guide mechanism 11, which is an example of a wire advancing/retracting mechanism of the endoscope 1, according to the embodiment of the present invention.

The guide mechanism 11 is configured to guide the treatment instrument T, which is inserted through the treatment instrument insertion opening 4a and introduced into the opening portion 6a, to a subject. The guide mechanism 11 includes a treatment instrument raising base 21, which is a movable portion, a distal end holding portion 31, a proximal end holding portion 41, an outer cylinder 51, a fixture 61, an inner cylinder 71, a wire 81, a coupler 91, a shaft 101, and an operation knob 111.

The treatment instrument raising base 21 is formed of, but not limited to, a material such as resin or metal. The treatment instrument raising base 21 is provided inside the opening portion 6a. The treatment instrument raising base 21 is raised or brought down with advancement/retraction of the wire 81. In other words, the treatment instrument raising base 21, which is provided on a distal end side of the insertion section 5, is configured to change an orientation of a distal end side of the treatment instrument T inserted in the insertion section 5. The treatment instrument raising base 21 has one end portion 22, the other end portion 23, and a guide surface 24.

The one end portion 22 is rotatably supported by a rotary shaft 22a provided on a bottom portion of the opening portion 6a.

The other end portion 23 is provided opposite the one end portion 22 in the treatment instrument raising base 21. The wire 81 is coupled to the treatment instrument raising base 21 at a predetermined position closer to the other end portion 23 than to the one end portion 22.

The guide surface 24 is provided between the one end portion 22 and the other end portion 23. To guide the treatment instrument T to a subject through the opening portion 6a, the guide surface 24 is disposed at a position where the treatment instrument T entering the inside of the opening portion 6a from the insertion section 5 comes into contact, the position being in the treatment instrument raising base 21 facing the opening portion 6a. The guide surface 24 may be in a curved concave shape to more smoothly guide the treatment instrument T to the subject.

The distal end holding portion 31 is formed of, but not limited to, a material such as resin or metal. The distal end holding portion 31 is provided continuous with an inner circumferential surface of the insertion section 5 near the distal end member 6, providing liquid-tight sealing between the insertion section 5 and the outer cylinder 51. The distal end holding portion 31, which is, for example, in an annular shape, holds the outer cylinder 51 and the inner cylinder 71 disposed inside.

The proximal end holding portion 41 is formed of, but not limited to, a material such as resin or metal. The proximal end holding portion 41 is provided at a proximal end portion of the operation section 4. The proximal end holding portion 41, which is, for example, in a cylindrical shape, holds the outer cylinder 51 disposed inside. The proximal end holding portion 41 may include, for example, a cylindrical metal fitting, an elastomer tube, and an external coil pipe. The proximal end holding portion 41 includes an outer circumferential wall 42, an inner circumferential wall 43, and a fitting groove 44.

The outer circumferential wall 42 is disposed in a circumferential direction adjacent to an outer circumferential surface of the outer cylinder 51. The outer circumferential wall 42 protects the outer cylinder 51 so that the outer cylinder 51 is not buckled by applied force.

The inner circumferential wall 43 is disposed in the circumferential direction adjacent to an inner circumferential surface of the outer cylinder 51. The inner circumferential wall 43 has an opening at each of an inner circumferential wall distal end portion 43a and an inner circumferential wall proximal end portion 43b. The inner circumferential wall distal end portion 43a is disposed on a proximal end side relative to an outer circumferential wall distal end portion 42a. The inner circumferential wall proximal end portion 43b extends outward, being coupled to an outer circumferential wall proximal end portion. An inner circumferential wall inner circumferential portion 43c communicates with the opening provided in a middle portion of each of the inner circumferential wall distal end portion 43a and the inner circumferential wall proximal end portion 43b.

The fitting groove 44, which is provided between the outer circumferential wall 42 and the inner circumferential wall 43, has a groove opening on a distal end side.

Note that although the proximal end holding portion 41 provides liquid-tight sealing between the operation section 4 and the outer cylinder 51 in FIG. 3, the proximal end holding portion 41 may be provided at a portion where an external liquid does not to enter within the operation section 4.

Figure 4:
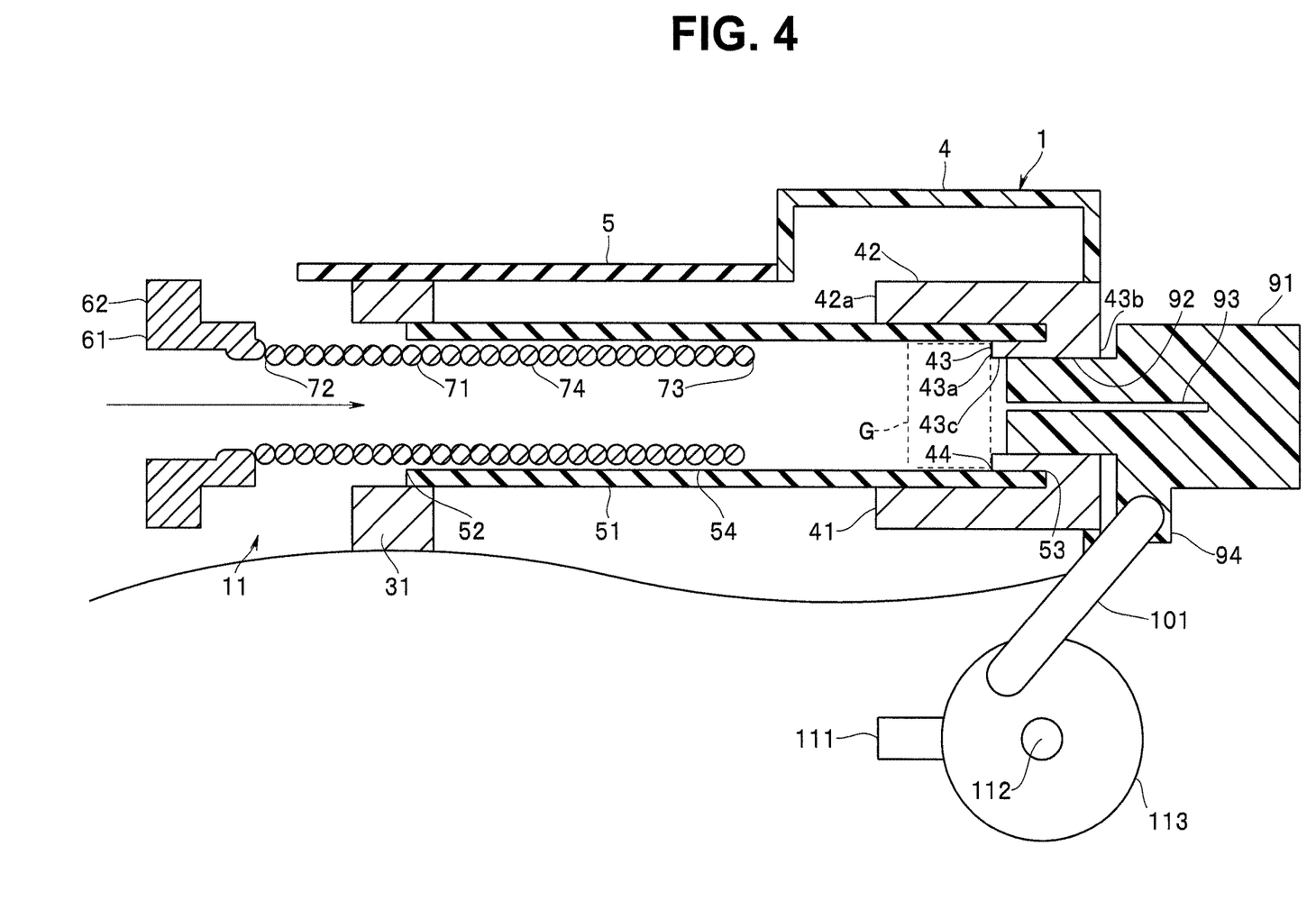
FIG. 4 is a diagram showing an attachment example of an inner cylinder of the guide mechanism of the endoscope according to the embodiment of the present invention.
Figure 5:
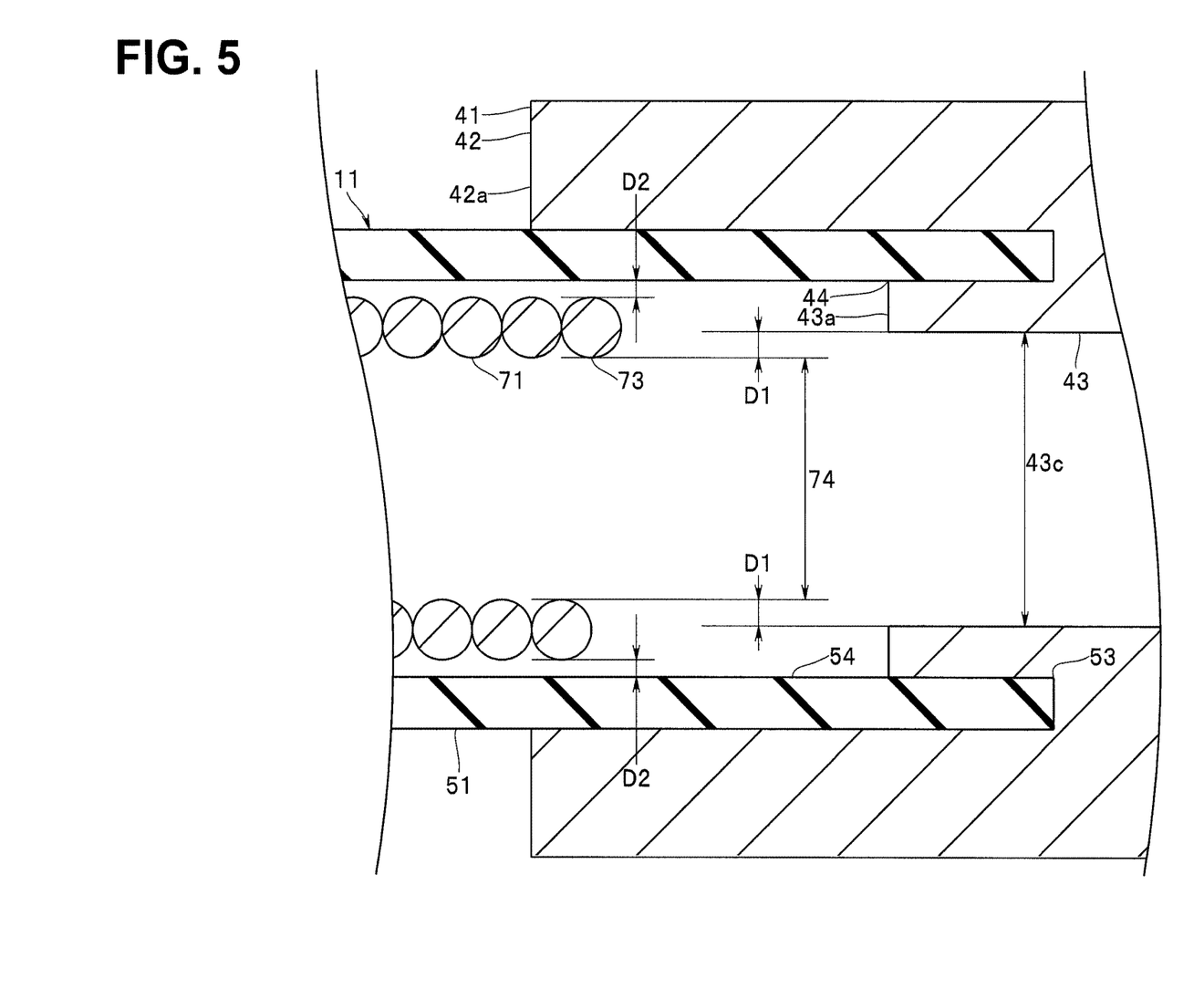
FIG. 5 is an explanatory diagram for explaining a structure of a proximal end holding portion, an outer cylinder, and the inner cylinder of the guide mechanism of the endoscope according to the embodiment of the present invention.
Figure 6:
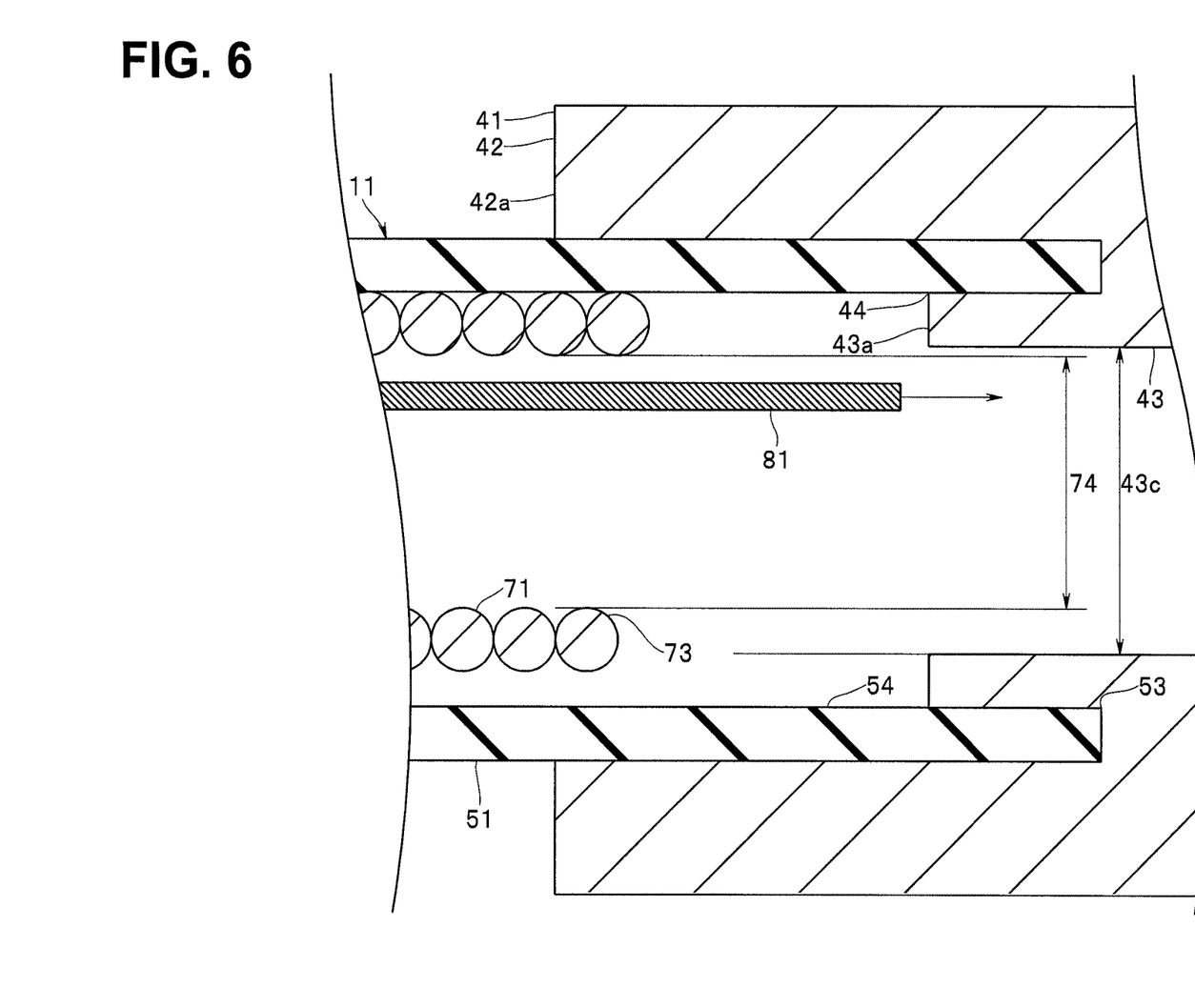
FIG. 6 is an explanatory diagram for explaining the structure of the proximal end holding portion, the outer cylinder, and the inner cylinder of the guide mechanism of the endoscope according to the embodiment of the present invention.

FIG. 4 is a diagram showing an attachment example of the inner cylinder 71 of the guide mechanism 11 of the endoscope 1 according to the embodiment of the present invention. FIG. 5 and FIG. 6 are each an explanatory diagram for explaining a structure of the proximal end holding portion 41, the outer cylinder 51, and the inner cylinder 71 of the guide mechanism 11 of the endoscope 1 according to the embodiment of the present invention.

The outer cylinder 51 includes, but not limited to, an elastic member such as a rubber tube. The outer cylinder 51 is held at an outer cylinder distal end portion 52 by the distal end holding portion 31 provided inside the insertion section 5 and held at an outer cylinder proximal end portion 53 by the proximal end holding portion 41 provided on a proximal end side relative to the distal end holding portion 31. The outer cylinder 51 extends in the operation section 4 and the insertion section 5, causing the operation section 4 and the insertion section 5 to communicate with each other.

The outer cylinder 51 has an opening at each of the outer cylinder distal end portion 52 and the outer cylinder proximal end portion 53. The outer cylinder distal end portion 52 is held inside the distal end holding portion 31. The outer cylinder proximal end portion 53 is held inside the proximal end holding portion 41. An outer cylinder inner circumferential portion 54 communicates with the opening of each of the outer cylinder distal end portion 52 and the outer cylinder proximal end portion 53. The outer cylinder proximal end portion 53 is fitted in the fitting groove 44.

The outer cylinder 51 is configured to be bent along with the insertion section 5. When the treatment instrument raising base 21 is pulled with the wire 81 or an external force is received in a proximal end direction from the distal end member 6 due to, for example, insertion of the insertion section 5 into a subject, the outer cylinder 51 contracts.

The fixture 61 is formed of, for example, but not limited to, metal. The fixture 61 is in a short-cylindrical shape, and respective openings provided at middle portions of a distal end surface and a proximal end surface communicate with each other. An outward flange 62 projecting externally in a radial direction is provided on a distal end side of the fixture 61. The fixture 61 is configured to fix the inner cylinder 71 to the distal end holding portion 31 and the outer cylinder 51.

The inner cylinder 71 is formed of, for example, but not limited to, metal. The inner cylinder 71 includes a member smaller in an amount of contraction due to an external force than the outer cylinder 51 so that the buckling of the outer cylinder 51 can be prevented. The inner cylinder 71 also includes a member larger in an amount of stretch due to bending than the outer cylinder 51. The inner cylinder 71 includes, for example, a tightly wound coil pipe.

The inner cylinder 71 is provided continuous with a proximal end side of the fixture 61. The inner cylinder 71 may be welded to the fixture 61. The inner cylinder 71 is disposed internally with respect to the distal end holding portion 31 and the proximal end holding portion 41 and inside the outer cylinder 51. The inner cylinder 71 has a predetermined cylinder length. The inner cylinder 71 has an opening at each of an inner cylinder distal end portion 72 and an inner cylinder proximal end portion 73. The inner cylinder proximal end portion 73 is disposed on a proximal end side relative to the outer circumferential wall distal end portion 42a. The inner cylinder 71 is configured to be bent along with the outer cylinder 51. The inner cylinder inner circumferential portion 74 communicates with the opening of each of the inner cylinder distal end portion 72 and the inner cylinder proximal end portion 73.

The inner cylinder 71 is removably attached to the outer cylinder 51. As shown in FIG. 4, the inner cylinder 71 is attached by inserting the inner cylinder 71 into the outer cylinder 51 through the opening of the outer cylinder distal end portion 52 until the outward flange 62 of the fixture 61 is stopped by contact with the distal end holding portion 31. Note that the inner cylinder 71 is removed from the outer cylinder 51 by pulling back the fixture 61.

The predetermined cylinder length is set by pre-adjustment such that a gap G is formed in the longitudinal direction between the inner cylinder proximal end portion 73 and the proximal end holding portion 41 when the fixture 61 provided on a distal end side of the inner cylinder 71 is attached to the outer cylinder distal end portion 52.

The predetermined cylinder length ranges from a length in a straight state of the inner cylinder 71 to a length in a maximum-bent-stretched state where the inner cylinder 71 is bent along with the insertion section 5 to stretch to the maximum. The predetermined cylinder length is set by pre-adjustment such that in a stretch state where the inner cylinder 71 is bent to stretch, more specifically, in the maximum-bent-stretched state, the gap G is formed in the longitudinal direction between the inner cylinder proximal end portion 73 and the proximal end holding portion 41.

The predetermined cylinder length is set by pre-adjustment such that the contraction of the outer cylinder 51 causes the inner cylinder 71 to move in the proximal end direction along with the distal end holding portion 31, going into a poking state between the distal end holding portion 31 and the proximal end holding portion 41.

Note that it is desirable that the gap G be formed inside the operation section 4 having a higher rigidity than the insertion section 5.

As shown in FIG. 5, a difference in inner diameter D1 between the inner circumferential wall 43 and the inner cylinder 71 is set by pre-adjustment such that the difference in inner diameter D1 is larger than a radial direction gap D2 between the outer cylinder 51 and the inner cylinder 71. As shown in FIG. 6, even in a case where the inner cylinder 71 is in contact with the outer cylinder inner circumferential portion 54, the inner cylinder inner circumferential portion 74 is disposed internally in the radial direction with respect to a position along the inner circumferential wall inner circumferential portion 43c, preventing the wire 81 from getting caught by the inner circumferential wall distal end portion 43a while being inserted.

As shown in FIG. 3, the wire 81 is formed of, but not limited to, metal such as stainless steel and may, as an example, be formed of a twisted wire including a plurality of metal wires. The wire 81 is provided inside the inner cylinder 71. The wire 81 is removably coupled to the treatment instrument raising base 21 at a distal end portion and removably coupled to the coupler 91 at a proximal end portion. In other words, the wire 81 is removably attached to the outer cylinder 51. The wire 81 is configured to be advanced or retracted by an external operation to raise or bring down the treatment instrument raising base 21. Note that the wire 81 may be rotatably fixed to the treatment instrument raising base 21 with the proximal end portion of the wire 81 removably coupled to the coupler 91 so that the wire 81 can be attached to/removed from the distal end member 6 and the outer cylinder 51 along with the treatment instrument raising base 21.

The coupler 91 is formed of, but not limited to, a material such as resin or metal. The coupler 91 is provided slidably in the longitudinal direction at the inner circumferential wall inner circumferential portion 43c. The coupler 91 couples the shaft 101 and the wire 81 to each other. The coupler 91 includes a piston cylinder 92, a wire fixture 93, and a shaft coupler 94.

The piston cylinder 92 is slidably provided inside the inner circumferential wall 43. The wire 81 is inserted through the inside of the piston cylinder 92. On an outer circumferential portion of the piston cylinder 92, an □-shaped ring that maintains liquid tightness between the outer circumferential portion and the inner circumferential wall 43 may be attached. An unshown cylinder may be provided between the inner circumferential wall inner circumferential portion 43c and the piston cylinder 92.

The wire fixture 93 is provided continuous with a proximal end side of the piston cylinder 92. The wire fixture 93 is configured to fix the wire 81 inserted through the inside of the piston cylinder 92. The wire fixture 93 may fix the wire 81 by pressing or by engagement.

The shaft coupler 94 is provided outside the coupler 91. The shaft 101 is rotatably coupled to the shaft coupler 94. When the shaft coupler 94 receives a power transmitted from the shaft 101, the coupler 91 advances/retracts in the longitudinal direction in response to the power.

The shaft 101 is formed of, for example, but not limited to, metal. The shaft 101, which couples the operation knob 111 and the shaft coupler 94 to each other, is configured to convert a rotary motion received from the operation knob 111 to a linear motion and transmit the linear motion to the shaft coupler 94.

The operation knob 111 is formed of, but not limited to, a material such as resin or metal. The operation section 4 is provided with the operation knob 111, which is rotatable around a center shaft 112. The operation knob 111 can be rotated by a user. The operation knob 111 may include a rotary disc 113 configured to rotate around the center shaft 112. The rotary motion inputted to the operation knob 111 is transmitted to the shaft 101.

(Operation of Guide Mechanism 11)

Subsequently, description will be made on an operation of the guide mechanism 11 of the endoscope 1.

Figure 7:
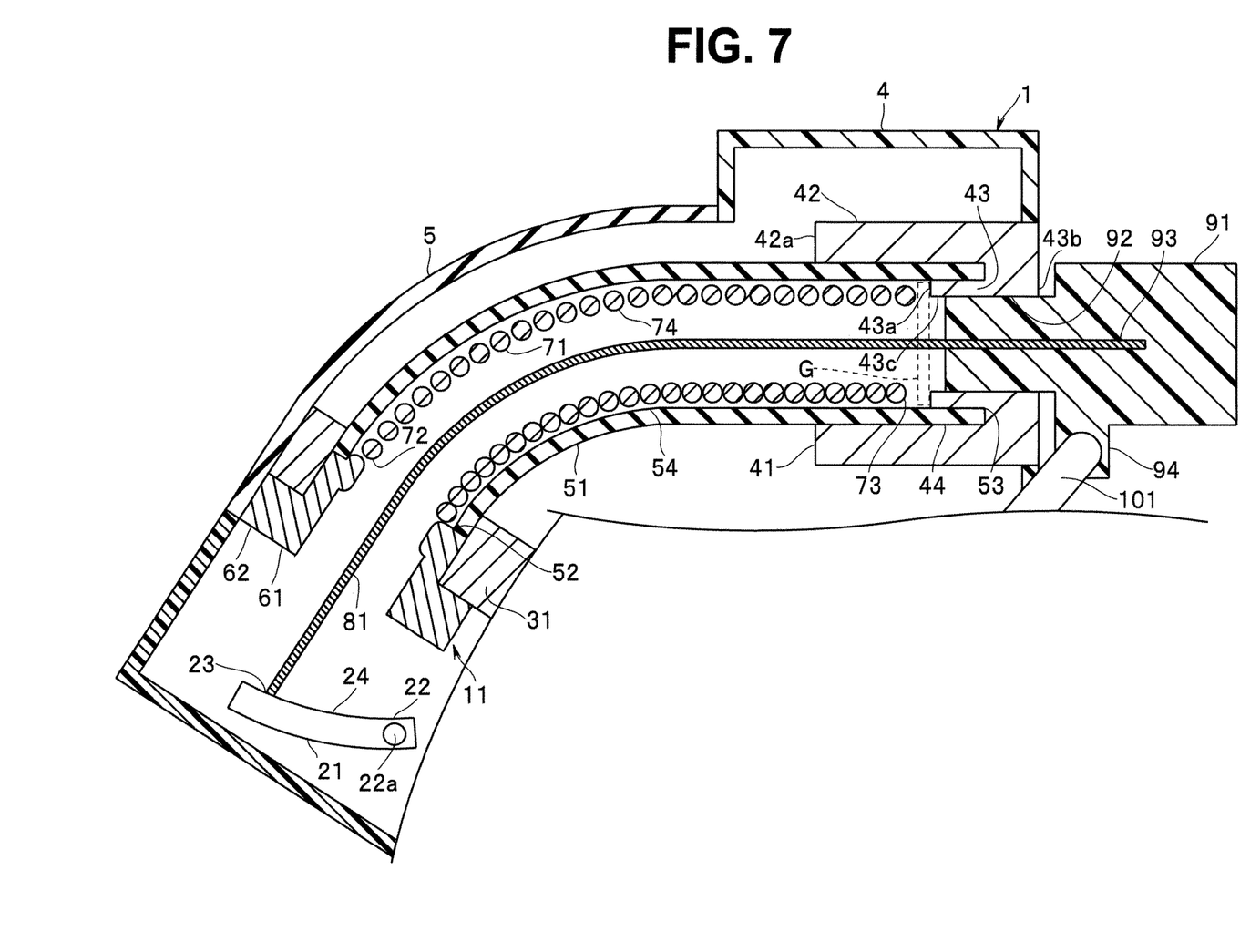
FIG. 7 is an explanatory diagram for explaining a state where the insertion section of the endoscope is bent according to the embodiment of the present invention.
Figure 8:
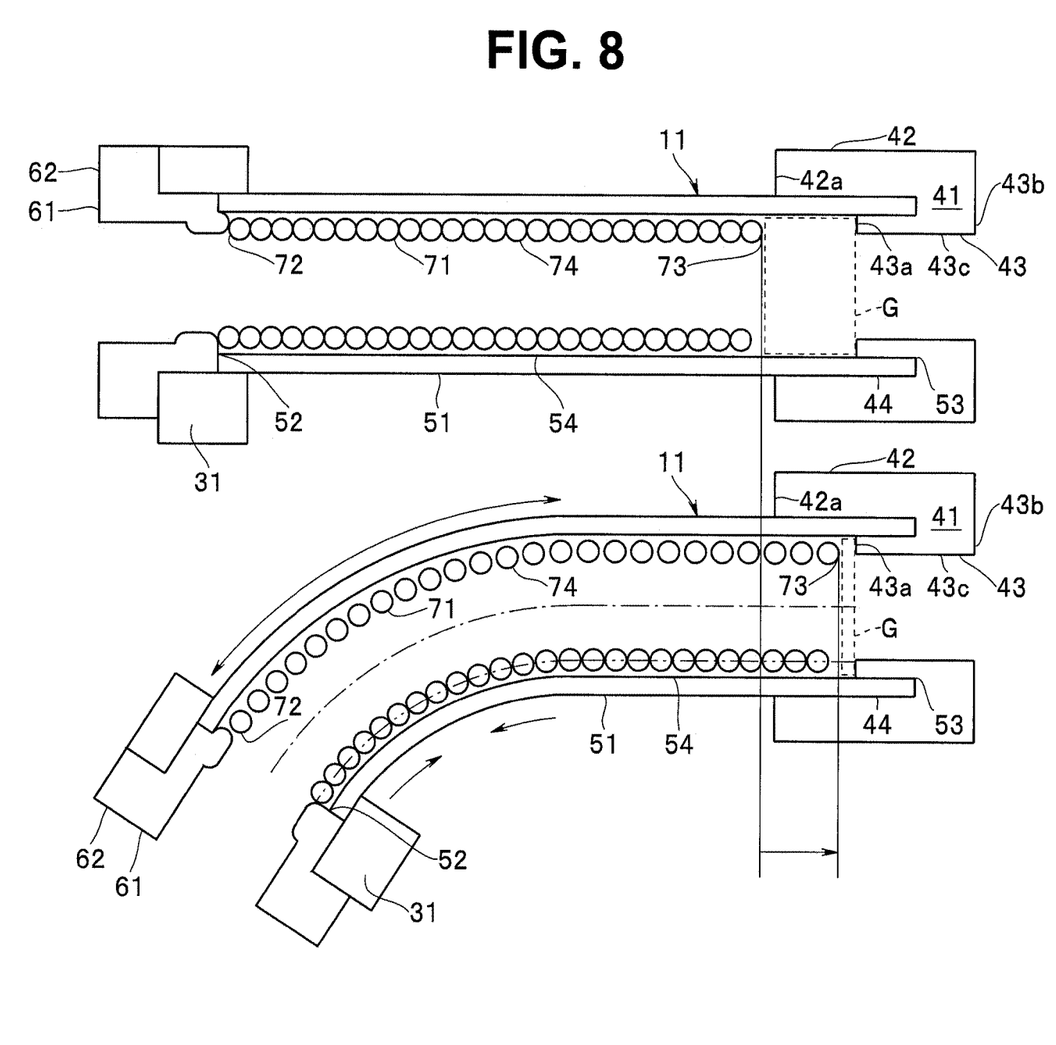
FIG. 8 is an explanatory diagram for explaining a difference in stretch due to bending between the outer cylinder and the inner cylinder of the endoscope according to the embodiment of the present invention.

FIG. 7 is an explanatory diagram for explaining a state where the insertion section 5 of the endoscope 1 is bent according to the embodiment of the present invention. FIG. 8 is an explanatory diagram for explaining a difference in stretch due to bending between the outer cylinder 51 and the inner cylinder 71 of the endoscope 1 according to the embodiment of the present invention.

As shown in FIG. 7, when the bending portion 5a and the insertion section 5 are bent by operating the angle knob 4b, the outer cylinder 51 and the inner cylinder 71 are also bent along with the insertion section 5.

As shown in FIG. 8, in the outer cylinder 51, with a neutral position defined substantially in a center portion in the radial direction as a reference, a bent inside portion contracts while a bent outside portion stretches (a chain line in FIG. 8). An amount of stretch of the outer cylinder 51 due to the bending of the insertion section 5 is smaller than an amount of stretch of the inner cylinder 71.

The inner cylinder 71, which includes the tightly wound coil, has a neutral position defined at substantially the same position as a bent inside portion (a two-dot chain line in FIG. 8). In the inner cylinder 71, the bent inside portion hardly contracts. In contrast, in the inner cylinder 71, a bent outside portion stretches due to a bending radius larger than a bending radius of the bent inside portion. The inner cylinder 71, the bent inside portion of which does not contract, stretches by a larger amount than the outer cylinder 51. When the outer cylinder distal end portion 52 and the inner cylinder distal end portion 72, each of which is held by the distal end holding portion 31, stretch due to bending, the inner cylinder proximal end portion 73 moves in the proximal end direction. With the gap G formed between the inner cylinder proximal end portion 73 and the proximal end holding portion 41, the inner cylinder 71 is prevented from going into the poking state and pressing the distal end member 6.

When a user pulls the wire 81 by operating the operation knob 111, an external force due to the pulling is transmitted to the outer cylinder 51 through the treatment instrument raising base 21, the distal end member 6, and the insertion section 5. When the external force causes the outer cylinder 51 to contract, the inner cylinder 71 comes into contact with the inner circumferential wall distal end portion 43a, going into the poking state between the distal end holding portion 31 and the proximal end holding portion 41 to support the outer cylinder 51 so that the outer cylinder 51 is not buckled. The treatment instrument raising base 21 and the distal end member 6 enable the inner cylinder 71 to go into the poking state when pulled with the wire 81, reliably reducing the possibility of occurrence of a defect such as fall of the inner cylinder 71. When the user cancels the pulling of the wire 81, the outer cylinder 51 restores due to an elastic force and, consequently, the poking state of the inner cylinder 71 between the distal end holding portion 31 and the proximal end holding portion 41 is also cancelled.

Therefore, in the endoscope 1, even in a case where the inner cylinder 71 stretches due to bending by a larger amount than the outer cylinder 51, the inner cylinder proximal end portion 73 enters the gap G to prevent the distal end member 6 from being pushed out by the inner cylinder 71. Even when the bending of the insertion section 5 causes the inner cylinder 71 to stretch by a larger amount than the outer cylinder 51, the guide mechanism 11 can reliably reduce the possibility of occurrence of a defect in the distal end member 6 of the insertion section 5.

According to the embodiment, the endoscope 1 includes the wire advancing/retracting mechanism with a reduced possibility of occurrence of a defect in the distal end member 6 of the insertion section 5 even when the insertion section 5 is bent.

(Modification 1 of Embodiment)

In the embodiment and other modifications, the outer circumferential wall 42 may be disposed adjacent to the outer circumferential surface of the outer cylinder 51, protecting the outer cylinder 51 so that the outer cylinder 51 is not buckled. However, the outer circumferential wall 42 and the outer cylinder inner circumferential portion 54 may be disposed adjacent to each other.

Figure 9:
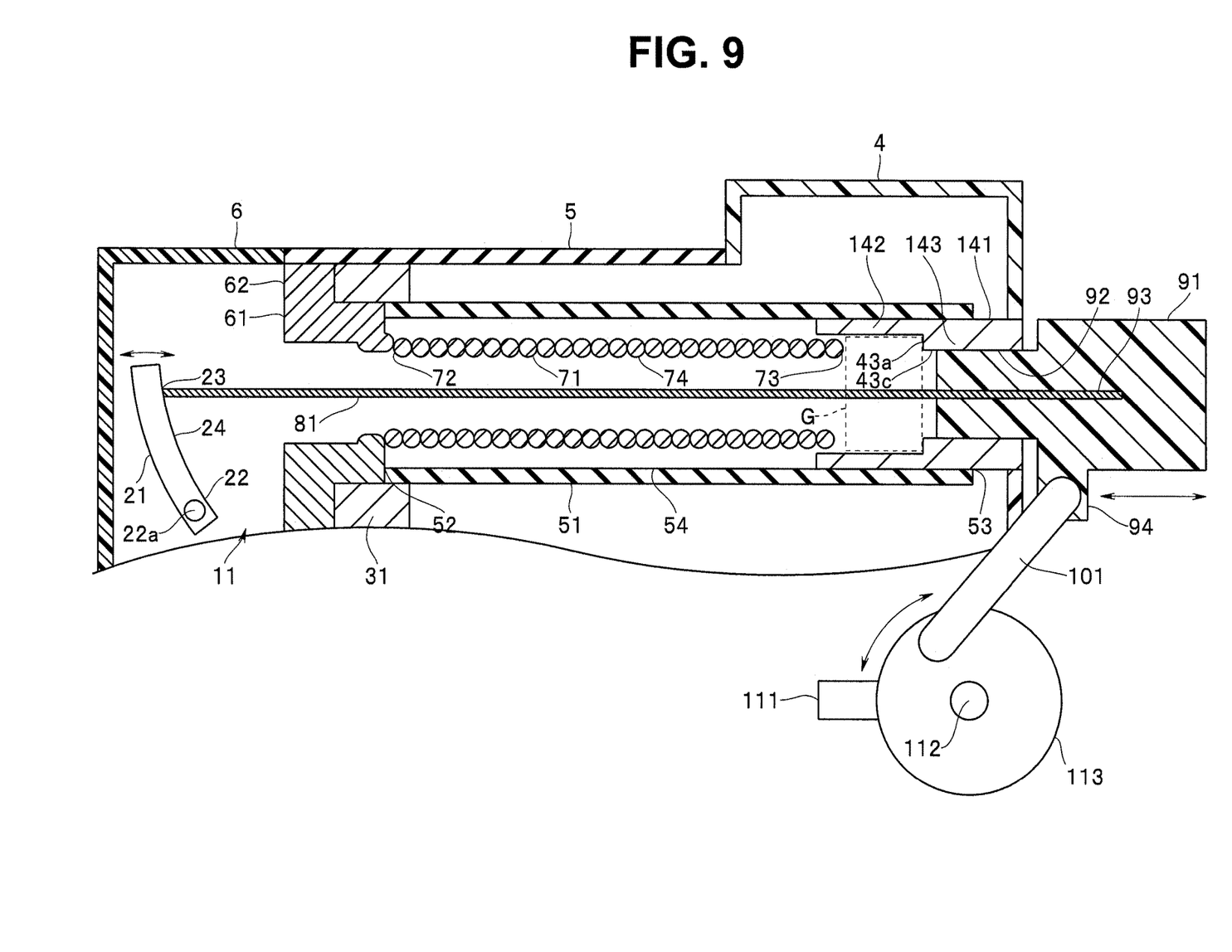
FIG. 9 is a diagram showing an example of the configuration of the guide mechanism of the endoscope according to Modification 1 of the embodiment of the present invention.

FIG. 9 is a diagram showing an example of the configuration of the guide mechanism 11 of the endoscope 1 according to Modification 1 of the embodiment of the present invention. In the present modification, description of the same components as in the embodiment and other modifications is omitted.

A proximal end holding portion 141 includes an outer circumferential wall 142 and an inner circumferential wall 143. The outer circumferential wall 142 and the inner circumferential wall 143 are integrated adjacent to each other.

The outer circumferential wall 142 is disposed in the circumferential direction adjacent to the outer cylinder inner circumferential portion 54. The outer circumferential wall 142 protects the outer cylinder 51 so that the outer cylinder 51 is not buckled.

The inner circumferential wall 143 is disposed in the circumferential direction adjacent to an outer circumferential surface of the piston cylinder 92.

In other words, the proximal end holding portion 141 is disposed inside the outer cylinder 51.

(Modification 2 of Embodiment)

In the embodiment and other modifications, the inner cylinder 71 includes no guide cylinder 261 at the inner cylinder proximal end portion 73. However, the guide cylinder 261 may be attached to the inner cylinder proximal end portion 73.

Figure 10:
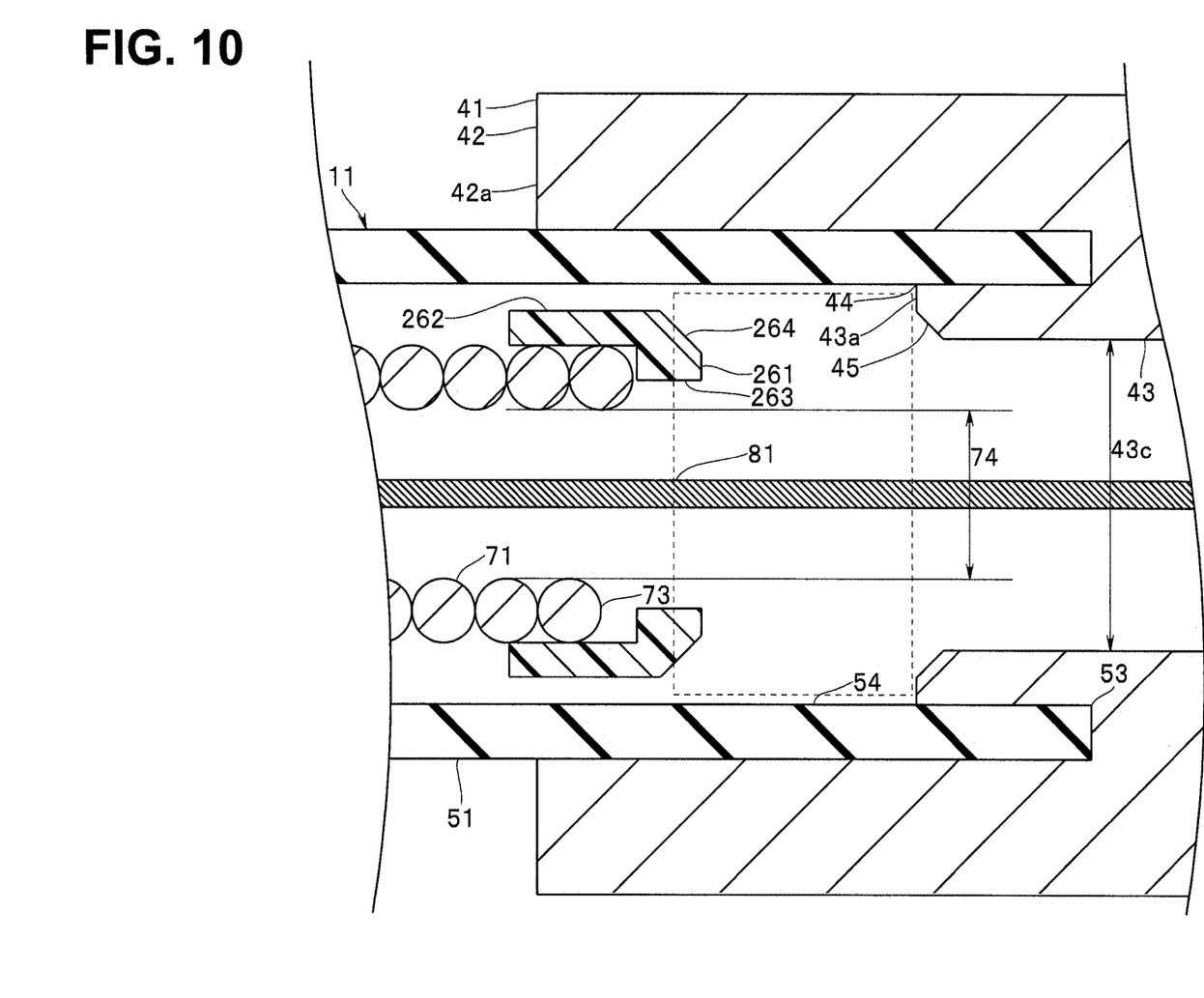
FIG. 10 is a diagram showing an example of the configuration of the guide mechanism of the endoscope according to Modification 2 of the embodiment of the present invention.

FIG. 10 is a diagram showing an example of the configuration of the guide mechanism 11 of the endoscope 1 according to Modification 2 of the embodiment of the present invention. In the present modification, description of the same components as in the embodiment and other modifications is omitted.

The proximal end holding portion 41 includes a guide receiver 45. The guide receiver 45, which is provided at an inner edge of the inner circumferential wall distal end portion 43a, is in a tapered shape increased in diameter toward a distal end direction.

The guide cylinder 261 is formed of, but not limited to, a material such as resin or metal. The guide cylinder 261 is provided at the inner cylinder proximal end portion 73. The guide cylinder 261 includes a cylinder wall 262 larger than the inner cylinder 71 so that the guide cylinder 261 can be attached to the inner cylinder proximal end portion 73. The guide cylinder 261 includes an inward flange 263 extending inward in the radial direction from a proximal end portion of the cylinder wall 262 and configured to be stopped by contact with the proximal end holding portion 41. The cylinder wall 262 includes a guide 264 in a tapered shape at an outer edge of the proximal end portion.

When the outer cylinder 51 contracts, the inner cylinder 71 moves in the proximal end direction. The guide of the guide cylinder 261 attached to the inner cylinder 71 comes into contact with the guide receiver 45, guiding the inner cylinder 71 inward in the radial direction with respect to the proximal end holding portion 41.

In other words, the guide cylinder 261, which is attached to the inner cylinder proximal end portion 73, includes the guide 264 in the tapered shape at the outer edge of the proximal end portion, and the proximal end holding portion 41 includes the guide receiver 45 in the tapered shape configured to guide the guide inward in the radial direction.

(Modification 3 of Embodiment)

In the embodiment and other modifications, the fixture 61 and the inner cylinder 71 are coupled to each other. However, the fixture 61 and the inner cylinder 71 may be separated from each other.

Figure 11:
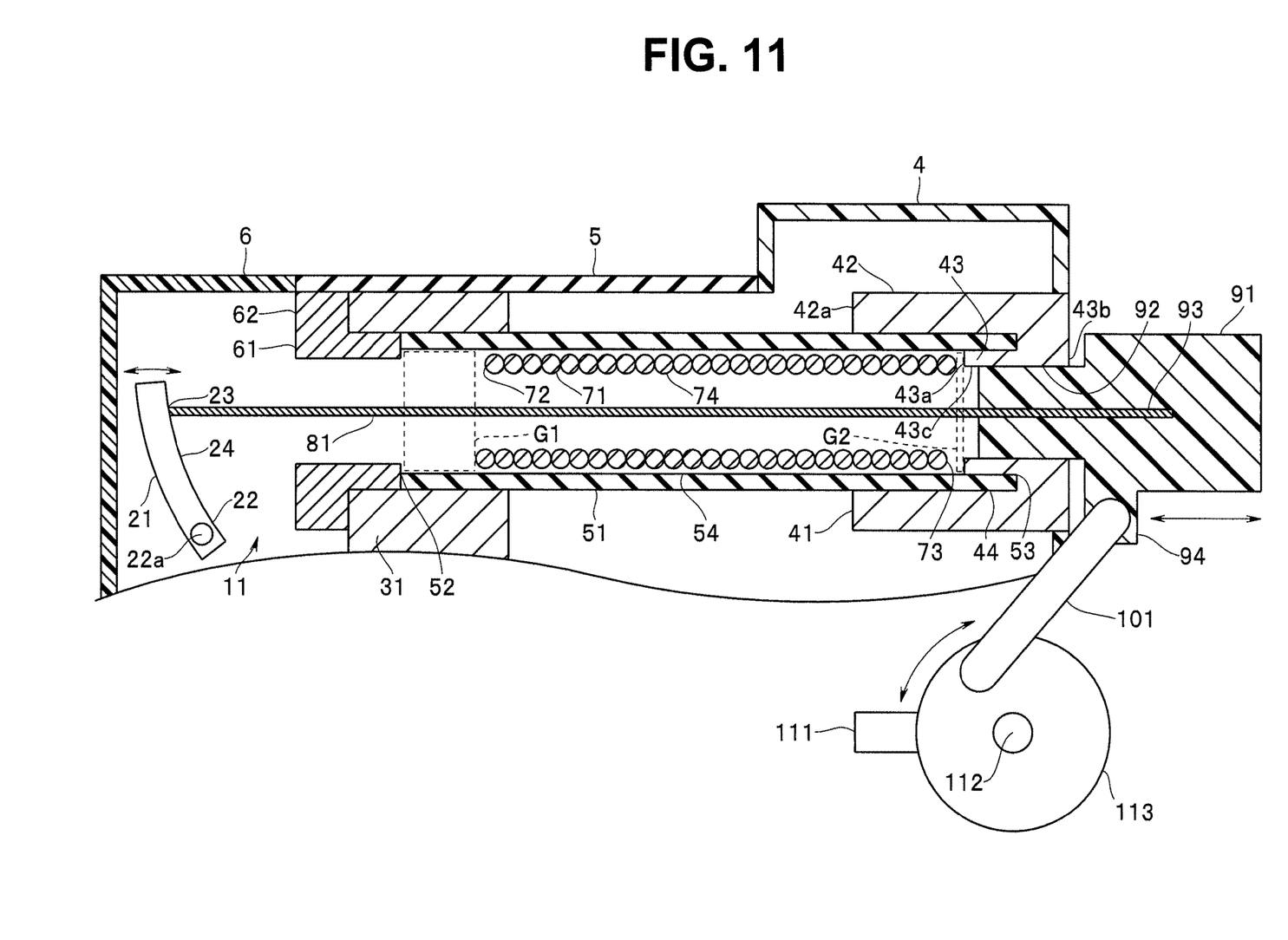
FIG. 11 is a diagram showing an example of the configuration of the guide mechanism of the endoscope according to Modification 3 of the embodiment of the present invention.

FIG. 11 is a diagram showing an example of the configuration of the guide mechanism 11 of the endoscope 1 according to Modification 3 of the embodiment of the present invention.

The fixture 61 and the inner cylinder 71 are separated from each other.

The predetermined cylinder length is set by pre-adjustment such that in the maximum-bent-stretched state, a gap G1 is formed in the longitudinal direction between the inner cylinder distal end portion 72 and the distal end holding portion 31 and a gap G2 is formed in the longitudinal direction between the inner cylinder proximal end portion 73 and the inner circumferential wall distal end portion 43a of the proximal end holding portion 41.

The endoscope 1 includes the fixture 61 separated from the inner cylinder 71. The fixture 61 is fixed to an end portion of the outer cylinder 51 and the distal end holding portion 31 with the gaps G1 and G2 formed between the inner cylinder 71 and the distal end holding portion 31 and between the inner cylinder 71 and the proximal end holding portion 41, respectively.

The inner cylinder 71 is provided inside the outer cylinder 51, and the inner cylinder 71 includes insider thereof the wire 81 coupled to the movable portion provided in the insertion section 5, the amount of stretch of the inner cylinder 71 due to the bending of the insertion section 5 is larger than the amount of stretch of the outer cylinder 51 due to the bending, and the cylinder 71, in the stretch state where the inner cylinder 71 stretches due to the bending, forms the gap G1 or G2 in the longitudinal direction of the outer cylinder 51 between the inner cylinder 71 and at least one of the distal end holding portion 31 or the proximal end holding portion 41.

More specifically, in the maximum-bent-stretched state where the inner cylinder 71 stretches to the maximum due to the bending, the inner cylinder 71 has the predetermined cylinder length allowing the gap G1 or G2 to be formed in the longitudinal direction of the outer cylinder 51 between the inner cylinder 71 and at least one of the distal end holding portion 31 or the proximal end holding portion 41.

Note that the configuration in which the inner cylinder 71 includes a coil pipe is described in the embodiment and the modifications, but this configuration is not limited to itself. The inner cylinder 71 may include a corrugate tube, bellows, a bellows cylinder, a hollow twisted pipe, a pipe including a plurality of coupled rings, a spiral tube, or the like.

Note that the inner cylinder 71 may be disposable.

Note that no member is disposed in any of the gaps G, G1, and G2 in the embodiment and the modifications, but another member such as a compression spring, a sponge, a stretching tube, or an elastic member may further be provided to guide the inner cylinder inward in the radial direction. A shape, a material, an elastic force, etc. of the member in any of the gaps G, G1, and G2 may be set by pre-adjustment such that the stretch of the inner cylinder 71 due to bending causes no defect in the distal end member 6 of the insertion section 5 to occur.

Note that the example of the guide mechanism 11 configured to guide the treatment instrument T of the endoscope 1 of the present invention is described in the embodiment and the modifications, but the wire advancing/retracting mechanism is not limited to the guide mechanism 11 described in the embodiment and the modifications. For example, the present invention may be applied to an endoscope including a zoom mechanism in which an optical system is a movable portion, an optical system moving mechanism in which a movable portion is configured to move an optical system, a hardness variable mechanism in which a movable portion is configured to pull an inner cylinder to enhance hardness, and a wire advancing/retracting mechanism functioning as a bending length variable mechanism in which a movable portion is configured to cause the stretch and contraction of a bend restricting cylinder to change a bending length.

The present invention is not limited to the above-described embodiment and a variety of modifications, alterations, etc. are possible unless they change the gist of the present invention.

What is claimed is:

1. An endoscope comprising:
    an insertion section extending in a longitudinal direction;
    a distal end holding member provided inside the insertion section;
    a proximal end member having a proximal end holding portion, the proximal end member being provided proximally relative to the distal end holding member;
    an outer cylinder including a distal end portion held by the distal end holding member and a proximal end portion held by the proximal end holding member; and
    an inner cylinder provided inside the outer cylinder;
    a treatment instrument raising base provided on a distal end side of the insertion section and configured to change an orientation of a distal end side of a treatment instrument inserted in the insertion section;
    a wire inserted into the inner cylinder and coupled to the treatment instrument raising base, the wire is configured to be advanced or retracted by an external operation to raise or lower the treatment instrument raising base; and
    wherein a gap is formed between a proximal end face of the inner cylinder and a corresponding surface of the proximal end member in the longitudinal direction at least when the inner and outer cylinders are bent together relative to the longitudinal direction; and
    a first difference between an inner diameter of the inner cylinder and the inner diameter of an inner circumferential wall of the proximal end member is larger than a second difference between an inner diameter of the outer cylinder and an outer diameter of the inner cylinder.

2. The endoscope according to claim 1, wherein the inner diameter of the inner cylinder is smaller than the inner diameter of the inner circumferential wall of the proximal end member.

3. The endoscope according to claim 1, further comprising a guide cylinder attached to a proximal end portion of the inner cylinder, the guide cylinder including a first tapered surface at a proximal end portion of the guide cylinder, wherein
    the proximal end member includes a second tapered surface configured to engage with the first tapered surface and guide the guide cylinder inward in a radial direction.

4. The endoscope according to claim 1, wherein
    the gap comprises a proximal gap; and
    a distal gap is formed between a distal end face of the inner cylinder and a corresponding surface of the distal end holding member in the longitudinal direction of the insertion section.

5. The endoscope according to claim 1, wherein
    the proximal end holding portion comprises a groove; and
    the proximal end portion of the outer cylinder is held in the groove.

6. The endoscope according to claim 1, wherein an amount of stretch of the inner cylinder due to bending of the inner and outer cylinders being larger than an amount of stretch of the outer cylinder due to the bending of the inner and outer cylinders.

7. An endoscope comprising:
    an operation section comprising a first holder, the first holder comprising an inner circumferential wall;
    an insertion section located distally relative to the operation section, the insertion section comprising a second holder located inside the insertion section;
    a first cylinder comprising:
        a first distal end attached to the second holder; and
        a first proximal end attached to the first holder;
    a second cylinder located inside the first cylinder; the second cylinder comprising:
        a second distal end; and
        a second proximal end spaced apart from the first holder in a longitudinal direction of the first cylinder;
    a movable base located inside a distal end side of the insertion section and configured to change an orientation of a distal end side of a treatment instrument inserted into the insertion section; and
    a wire inserted into the second cylinder and coupled to the movable base, the wire configured to be advanced or retracted,
    wherein a first difference between a first inner diameter of the second cylinder and a second inner diameter of the inner circumferential wall is larger than a second difference between a third inner diameter of the first cylinder and an outer diameter of the second cylinder.

8. The endoscope according to claim 7, wherein the first inner diameter of the second cylinder is smaller than the second inner diameter of the inner circumferential wall.

9. The endoscope according to claim 7, further comprising a guide cylinder attached to the second proximal end of the second cylinder, the guide cylinder including a first tapered surface at a proximal end portion of the guide cylinder,
    wherein the first holder includes a second tapered surface configured to engage with the first tapered surface and guide the guide cylinder inward in a radial direction.

10. The endoscope according to claim 7, wherein the second distal end of the second cylinder is spaced apart from the second holder in the longitudinal direction.

11. The endoscope according to claim 7, wherein
    the first holder comprises a groove; and
    the first proximal end of the first cylinder is held in the groove.

12. The endoscope according to claim 7, wherein the second proximal end of the second cylinder is located inside the operation section.

13. The endoscope according to claim 7, wherein the second proximal end of the second cylinder is located inside the operation section when the insertion section is bent relative to the longitudinal direction.

14. The endoscope according to claim 7, wherein the second proximal end of the second cylinder is located proximally relative to a distal end of an outer circumferential wall of the first holder.

15. The endoscope according to claim 7, wherein the first holder comprises an inner circumferential portion comprising:
the inner circumferential wall; and
a distal end wall intersecting the inner circumferential wall,
wherein the distal end wall is spaced apart from the second proximal end in the longitudinal direction.

16. The endoscope according to claim 7, wherein the second distal end of the second cylinder is attached to the second holder.

17. The endoscope according to claim 7, wherein the second distal end of the second cylinder is spaced apart from the second holder.

18. The endoscope according to claim 7, wherein
the insertion section is deformable between a straight state and a bent state,
in the straight state, a proximal end face of the second cylinder is spaced apart from a corresponding surface of the first holder by a first gap in the longitudinal direction,
in the bent state, the proximal end face of the second cylinder is spaced apart from the corresponding surface of the first holder by a second gap in the longitudinal direction, the second gap is smaller than the first gap.

19. An endoscope comprising:
an operation section comprising a first holder, the first holder comprising an inner circumferential wall;
an insertion section located distally relative to the operation section, the insertion section comprising a second holder located inside the insertion section;
a first cylinder comprising:
a first distal end attached to the second holder; and
a first proximal end attached to the first holder;
a second cylinder located inside the first cylinder; the second cylinder comprising:
a second distal end; and
a second proximal end spaced apart from the first holder in a longitudinal direction of the first cylinder;
a movable base located inside a distal end side of the insertion section and configured to change an orientation of a distal end side of a treatment instrument inserted into the insertion section; and
a wire inserted into the second cylinder and coupled to the movable base, the wire configured to be advanced or retracted, wherein
a first inner diameter of the second cylinder is smaller than a second inner diameter of the inner circumferential wall.

20. The endoscope according to claim 19, wherein
wherein the first holder comprises an inner circumferential portion comprising:
the inner circumferential wall; and
a distal end wall intersecting the inner circumferential wall,
wherein the distal end wall is spaced apart from the second proximal end in the longitudinal direction.

* * * * *